United States Patent [19]
Whitehouse

[11] Patent Number: 5,944,803
[45] Date of Patent: Aug. 31, 1999

[54] ISOLATABLE MULTI-POINT SERIAL COMMUNICATION UTILIZING A SINGLE UNIVERSAL ASYNCHRONOUS RECEIVER AND TRANSMITTER (UART)

[75] Inventor: James B. Whitehouse, Brea, Calif.

[73] Assignees: Sony Corporation, Tokyo, Japan; Sony Trans Com Inc., Irvine, Calif.

[21] Appl. No.: 08/824,199

[22] Filed: Mar. 25, 1997

[51] Int. Cl.⁶ .................................................. G06F 13/14

[52] U.S. Cl. ........................... 710/63; 379/156; 379/164; 379/165

[58] Field of Search .................................. 379/164, 156, 379/165; 395/883; 710/63

[56] References Cited

U.S. PATENT DOCUMENTS

| | | | |
|---|---|---|---|
| 3,921,138 | 11/1975 | Burns et al. | 340/147 R |
| 4,100,533 | 7/1978 | Napolitano et al. | 340/147 R |
| 4,942,319 | 7/1990 | Pickett et al. | 307/465 |
| 4,998,275 | 3/1991 | Braunstein et al. | 379/164 |
| 5,123,015 | 6/1992 | Brady, Jr. et al. . | |

*Primary Examiner*—Thomas C. Lee
*Assistant Examiner*—Abdelmoniem L. Elamin
*Attorney, Agent, or Firm*—Blakely, Sokoloff, Taylor & Zafman LLP

[57] ABSTRACT

A communication interface circuit in an aircraft entertainment system uses a single Universal Asynchronous Receiver and Transmitter (UART) for sending and receiving data to and from a number of devices. The UART is coupled to a number of transceivers each having a transmitter buffer and a receiver buffer. A circuit is used to enable and disable the receiver buffers. A masking element is coupled between the receiver buffers and the UART to mask off the data from the disabled receiver buffers allow only the data from the enabled receiver buffer to go to the UART. With this communication interface circuit, the amount of hardware is significantly reduced.

20 Claims, 5 Drawing Sheets

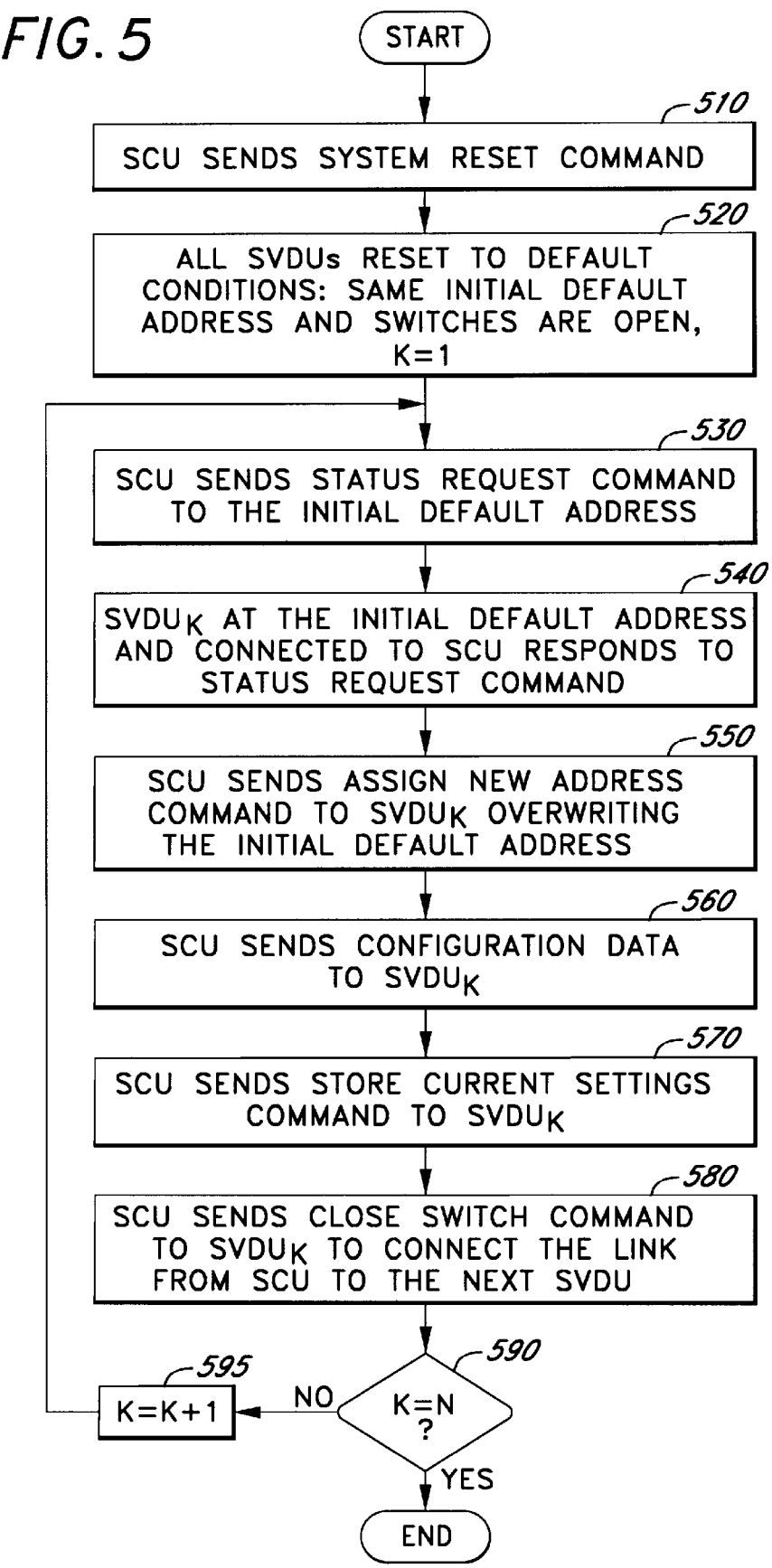

5,944,803

ISOLATABLE MULTI-POINT SERIAL COMMUNICATION UTILIZING A SINGLE UNIVERSAL ASYNCHRONOUS RECEIVER AND TRANSMITTER (UART)

BACKGROUND OF THE INVENTION

1. Field of the Invention

The present invention relates to architecture of a serial communication circuit used in In-Flight Entertainment Systems on aircraft. In particular, the present invention relates to the use of a single Universal Asynchronous Receiver and Transmitter (UART) in a multipoint communication to reduce hardware utilization.

2. Description of Related Art

In-Flight Entertainment Systems (IFES) are now becoming popular on commercial aircraft. A typical new IFES may offer a variety of services including music, news, movies, video on demand, telephone, and games to passengers right at the passengers' seats with the convenience of individualized control. A timetable is generally provided from which a passenger may choose options when he or she requests services. Such a system involves a large number of interconnections to various peripheral subsystems. The communication between these subsystems and the main processor (or the host processor) can be quite complex. A host processor, referred to as a System Control Unit (SCU), communicates with a large number of external Line Replacement Units (LRUs) for various operational and control functions, such as overhead display, video and audio control. To facilitate the communication between the display units and the control units, multipoint serial communication is employed. The serial communication among these units typically requires a large number of Universal Asynchronous Receiver and Transmitters (UARTs).

The serial communication in an IFES environment may consist of a number of UARTs at the SCU communicating with a number of UARTs at the LRUs through a number of transceivers. In one known system, multiple transceivers of the UARTs at the LRUs are tied together to form a single communication link to one transceiver of the UART at the control unit. The problem with this system is that it does not support isolatable topology of serial communication. Isolated serial links for command are important for a number of reasons. The first reason is increased fault tolerance: a failure of one transceiver in one communication link does not have any effect on the remaining links. The second reason is that the SCU can send individual control information, if desired, to each of the UARTs instead of broadcasting to all of them. The third reason is that isolatable topology provides flexibility in routing the connections.

Another way to provide isolatable serial communication links employs N UARTs at the control unit, one for each of the N UARTs at the display units. This method, however, requires a large number of UARTs and transceivers at the SCU. In a typical IFES environment, this number could be prohibitively high. In addition, since each UART has its own input/output (I/O) address, the I/O address space to accommodate these devices may not be sufficient, especially when embedded control microprocessors or microcontrollers with limited I/O address space are employed.

It is therefore desirable to have a serial communication system in an IFES environment which provides isolatable serial communication link between the System Control Unit and the display units at the passenger's seats, and at the same time occupies as few I/O addresses as possible.

SUMMARY OF THE INVENTION

In an In-Flight Entertainment Systems (IFES), a communication interface circuit provides multipoint serial communication links from the System Control Unit (SCU) to a number of Video Display Units. The interface circuit consists of Universal Asynchronous Receivers/Transmitters (UARTs) with corresponding transceivers. At the System Control Unit, one UART is coupled to a number of transceivers which are connected to the transceivers at the Video Display Units to provide isolatable communication links.

At the System Control Unit, the receiver buffers at the transceivers are gated to provide a single line to the receiver of the SCU UART. One UART at the SCU can send control information to each of the UARTs at the Smart Video Distribution Units individually and receive status information from them. The present invention therefore eliminates the need for multiple UARTs at the SCU, resulting in reduced hardware and more reliability.

BRIEF DESCRIPTION OF THE DRAWINGS

The objects, features and advantages of the present invention will become apparent from the following detailed description of the present invention in which:

FIG. 5 is a flowchart illustrating one embodiment of the auto-configuration communication protocol between the SCU and the SVDUs.

DESCRIPTION OF THE PRESENT INVENTION

The present invention discloses a circuit used in in-flight entertainment systems (IFES) for multipoint serial communication. A single UART is used at the System Control Unit (SCU). Isolatable serial communication links are provided between the transmitter of the SCU UART and the receivers of the Smart Video Distribution Unit (SVDU). The receiver buffers at the SCU are gated to provide a single input to the receiver of the SCU UART. Since there is only one UART at the SCU which can communicate with a number of SVDUs, the amount of communication interface hardware at the SCU is reduced significantly.

In the following description, for purposes of explanation, numerous details are set forth, such as flowcharts and system configurations, in order to provide a thorough understanding of the present invention. However, it will be apparent to one skilled in the art that these specific details are not required in order to practice the present invention. In other instances, well known electrical structures and circuits are shown in block diagram form in order not to unnecessarily obscure the present invention.

Figure 1:
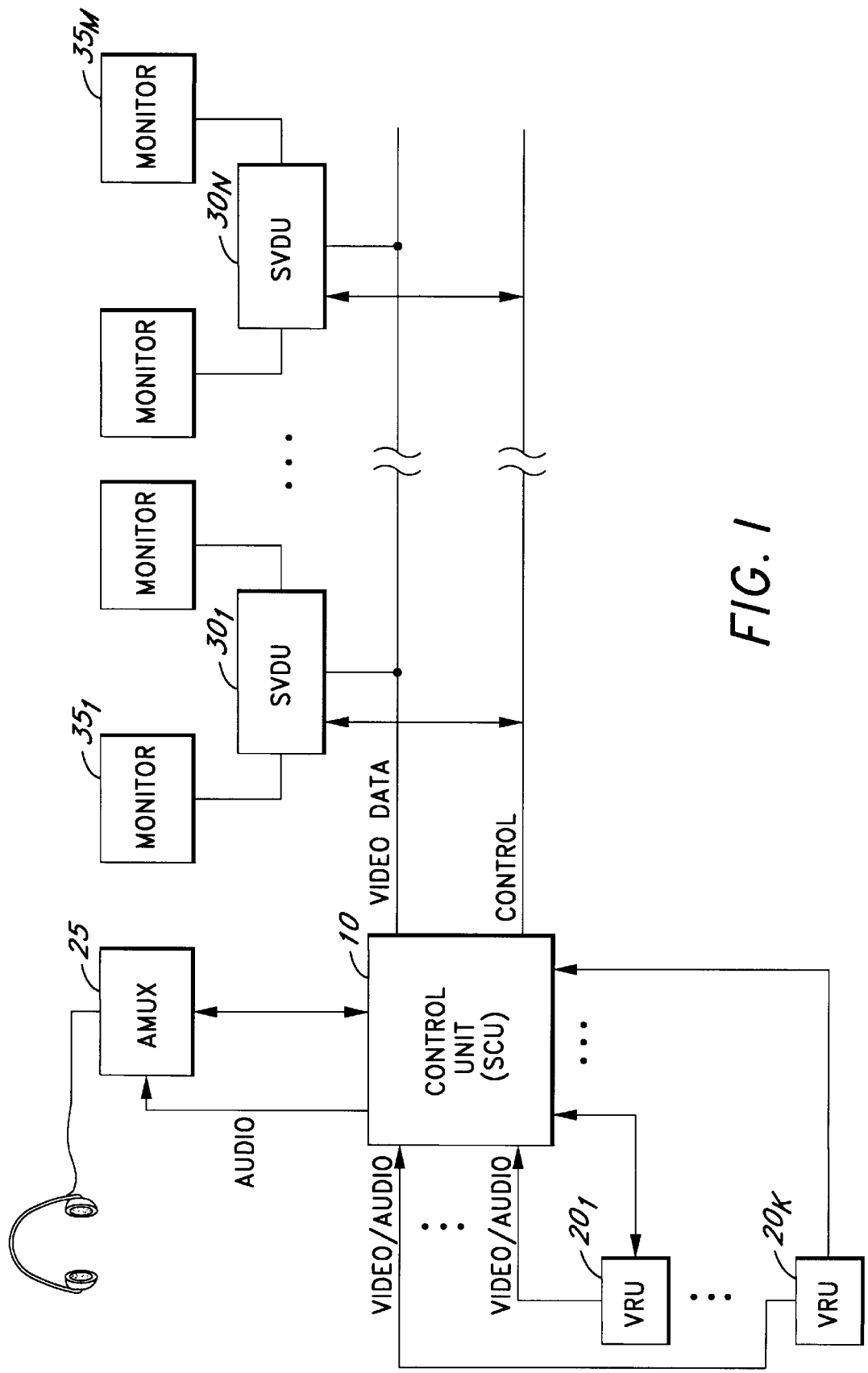
FIG. 1 is a block diagram illustration of one embodiment of a system that operates in accordance with the teachings of the present invention.

FIG. 1 is an illustration of one embodiment of the present invention. The IFES includes System Control Unit (SCU) 10 which controls many of the basic operations of the IFES. These operations are associated with the controlling and monitoring of a number of video and audio entertainment devices and/or subsystems installed at the passengers' seats. Some examples of these subsystems, or external devices, are Video Receiver Units (VRUs) $20_1$ through $20_K$, Audio Multiplexer Unit (AMUX) 25, and Smart Video Distribution Units (SVDU) $30_1$ through $30_N$. Each $SVDU_i$ in turn is connected to a number of display monitors $35_1$ through $35_M$.

The VRU is a video tape recorder/player that is used to produce video programs recorded in video tapes. The control and monitor operations for the VRU include stop, start, fast forward, rewind, etc. These control and monitor operations are carried out through the communication pathway connecting the VRU and the UART. Typically, there are a multiple of VRUs available to allow the operator/flight attendant to select the desired video programs.

The AMUX is an audio system having a multiple compact disks (CDs) players or the like to play prerecorded audio programs such as music, news, discussions, advertisements, etc. The AMUX is connected to a corresponding UART through a communication pathway carrying control and monitor signals from SCU 10. Each CD on an AMUX corresponds to an audio channel. A passenger can select the desired audio channel at his or her seat. Typical control and/or monitor operations for the AMUX include the selection of a particular track on a particular CD, the control of volume, the selection of filtering frequencies for sound enhancement, etc.

The SVDU controls a plurality of retractable overhead video monitors. The SVDU displays the selected video programs from the VRU on the selected video monitor. The control operations of the SVDU include selection of the video input channel, color enhancement, monitor deployment, monitor power control, etc. These operations are performed through the communication pathway connecting the SVDU with the corresponding UART.

The control and monitor operations are carried out by the transfer of messages between SCU 10 and these devices through serial communication links between them.

Figure 2:
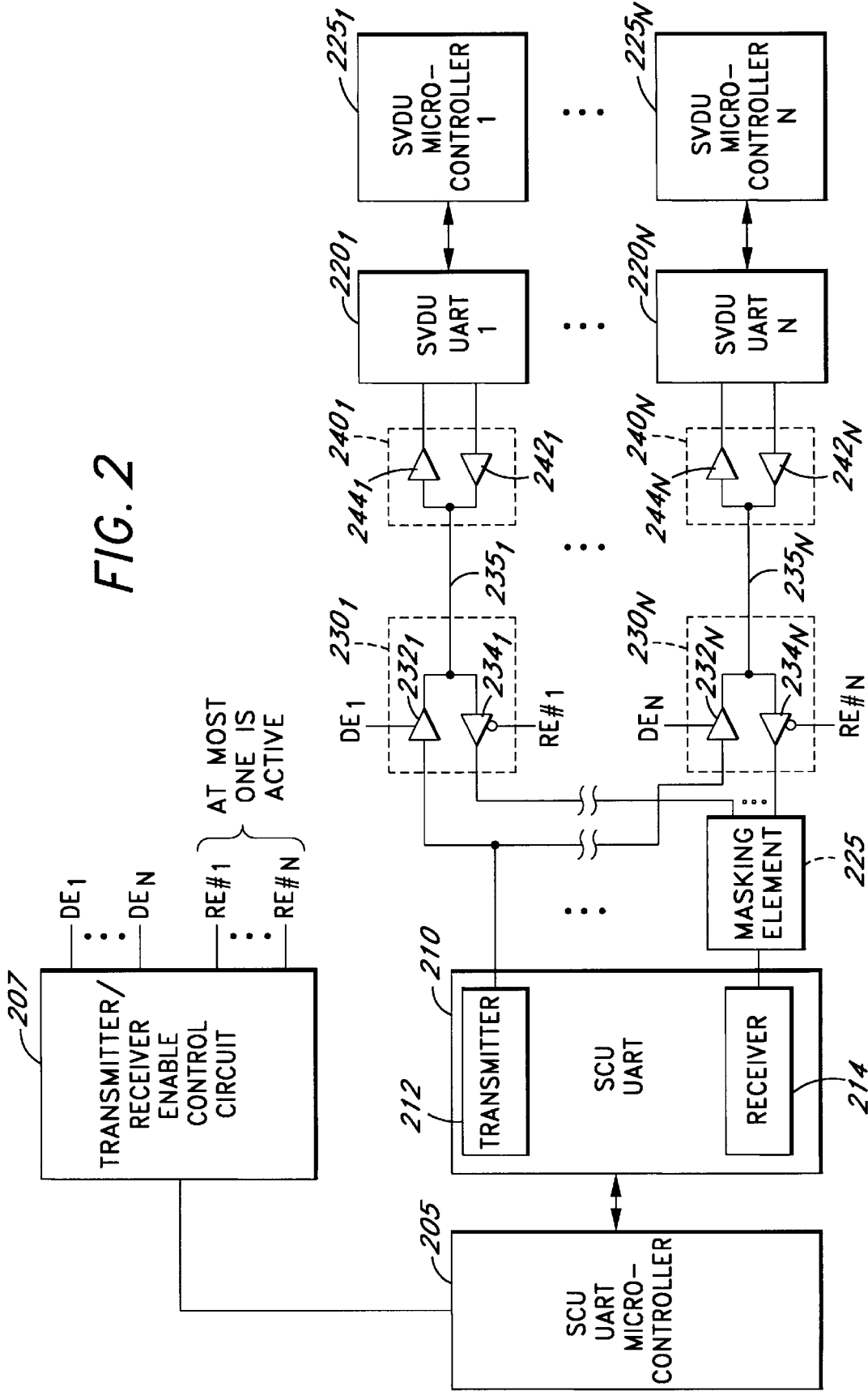
FIG. 2 shows one embodiment of the interfacing configuration having one SCU UART and N Video Display Unit UARTs.

FIG. 2 shows one embodiment of the present invention. The System Control Unit (SCU) may have several processors to perform dedicated tasks under the control and supervision of a master processor (not shown). SCU UART Microcontroller 205 is one of these processors which is responsible for the control of SCU UART 210. SCU UART 210 is used to transmit command from SCU UART Microcontroller 205 to the SVDUs, and receive messages from the SVDUs. SVDU UARTs $220_1$ to $220_N$ respond to the SCU UART Microcontroller commands by sending messages through the corresponding communication links $235_1$ to $235_N$. In one embodiment, these UARTs have a buffer queue at the receiver and transmitter to minimize receiver overrun and transmitter underrun. Examples of the UARTs used are the Dual UART (Part No. SC26C92) and Quad UART (Part No. SC2694) manufactured by Philips Semiconductor of Pleasanton, Calif.

In one embodiment, SCU UART Microcontroller 205 is a single-chip microcontroller, Part No. 87C51FB, manufactured by Intel Corporation at Santa Clara, Calif. Similarly, SVDU UARTs $220_1$ to $220_N$ are controlled by SVDU Microcontrollers $225_1$ to $225_N$, respectively. In one embodiment, SVDU Microcontrollers $225_1$ to $225_N$ are single-chip microcontrollers, Part No. 87C51FB, manufactured by Intel Corporation at Santa Clara, Calif.

The transmitter 212 of the SCU UART 210 is connected to the driver inputs of SCU transceivers $230_1$ to $230_N$ which form N serial communication links $235_1$ to $235_N$ connecting to SVDU transceivers $240_1$ to $240_N$ at the SVDUs, respectively. SVDU transceivers $240_1$ to $240_N$ are in turn interfaced to SVDU UARTs $220_1$ to $220_N$, respectively. SCU transceivers $230_1$ to $230_N$ contain SCU transmitter buffers $232_1$ to $232_N$ and SCU receiver buffers $234_1$ to $234_N$. SVDU transceivers $240_1$ to $240_N$ contain SVDU transmitter buffers $242_1$ to $242_N$ and SVDU receiver buffers $244_1$ to $244_N$, respectively. Each transmitter buffer is controlled by a Driver Enable (DE) signal. When DE is HIGH the driver buffer is enabled allowing the data at its input to pass through. When DE is LOW, the driver buffer is disabled, putting the driver buffer output in High Impedance (Hi-Z). Each receiver buffer is controlled by a Receiver Enable Low (RE#) signal. When RE# is asserted LOW, its receiver buffer is enabled, allowing the data at its input to pass through. When RE# is deasserted HIGH, its receiver buffer is disabled, setting the corresponding receiver output in high impedance. There are a number of ways to control the DE/RE# signals. One way is to use the Input/Output (I/O) ports from SCU UART microcontroller 205 to provide overriding/enable/disable control of the DE/RE# signals. In one embodiment, the DE/RE# signals are connected to the UART with logic to provide the microcontroller the ability to override the UART.

As will be discussed later, the control of SCU transceivers $230_1$ to $230_N$ establishes the communication protocol between the SCU and the SVDUs. The SCU can send a command to a specified SVDU or broadcast to all SVDUs. In return, the SVDUs respond to the SCU command one at a time. The communication protocol, to be described later, allows the exchange of commands/messages between the SCU and the SVDUs in a master-slave protocol. Under this protocol, at any time, only one SVDU responds to the SCU command. Therefore, at any time, at most one receiver buffer is enabled. The individual DE/RE# signals are controlled by SCU UART microcontroller 205 through the Transmitter/Receiver Enable Control Circuit 207. There are several ways to implement the Transmitter/Receiver Enable Control Circuit 207. One way is to connect the input/output (I/O) lines from the I/O expanders directly, one I/O line for each DE/RE# signal. The software creates bit patterns to ensure that the proper DE/RE# signals are deasserted to disable the corresponding transmitters/receivers. Another way is to connect the DE/RE# signals to the output lines of an k-to-$2^k$ decoder where N=$2^k$. Using the k-to-$2^k$ decoder would assure that at most one transmitter/receiver buffer is enabled.

In one embodiment, transceivers $230_1$ to $230_N$ and $240_1$ to $240_N$ are differential bus transceivers (Part No. SN65ALS176) manufactured by Texas Instruments of Dallas, Tex. The differential bus transceivers are designed for bidirectional data communication on multipoint bus transmission lines. They have both transmitter buffers and receiver buffers with the DE and RE# control signals as described above. Furthermore they also meet the Electronic Industry Association (EIA) Standards RS-422A and RS-485.

The receiver outputs of transceivers $230_1$ to $230_N$ are connected to the input lines of Masking Element 225. The output of Masking Element 225 is connected to Receiver 214 of SCU UART 210. Masking Element 225 essentially allows only the output of the enabled receiver buffer of transceivers $230_1$ to $230_N$ to pass through to Receiver 214 of SCU UART 210.

There are several ways to implement Masking Element 225. In one embodiment, Masking Element 225 is an N-input AND gate. A disabled receiver buffer output is interpreted as a logical "1" by the AND gate, essentially masking itself off, because a logical "1" input to an AND gate does not affect the output. This can be achieved by a number of methods. In one embodiment, the RE# signals at receiver buffers are used to set the corresponding receiver buffer outputs at appropriate level. When RE# is asserted LOW, the receiver buffer output is enabled transferring the logical value at its input. When RE# is negated HIGH, the receiver buffer output is in high impedance (Hi Z). A Hi Z input is interpreted as a logical "1" for transistor-transistor-logic (TTL) compatible gates such as AND gate 225. Another method that can be employed to produce a logical "1" for a disabled receiver is to use an open collector output having a pull-up resistor with an appropriate value. Similarly, Masking Element 225 may be implemented as an N-input OR gate if the disabled receiver buffer output is interpreted as a logical "0".

Another way to implement Masking Element 225 is to tie all the outputs of the receiver buffers of SCU transceivers together to form a tri-state bus. By controlling the RE# signals as described above such that at most one RE# signal is asserted (or at most one receiver buffer is enabled), the tri-state bus transfers the received data from the enabled buffer to Receiver 214 of SCU UART 210.

SCU UART microcontroller 205 has two addressing modes to address the SVDUs: broadcast and individual. In broadcast addressing, the command sent by SCU UART microcontroller 205 is sent to all SVDUs. Each SVDU is assigned a universal common address to respond to this broadcast addressing command. This broadcast capability provides a fast way for the SCU to communicate with all SVDUs at the same time in instances where immediate action is necessary such as power shutoff in response to cabin decompression. Since all SVDUs receive the same command, it is not required that SVDUs send responses back to the SCU. In individual addressing, the SCU sends a command to a specified SVDU. Each SVDU responds to its unique assigned individual address. This individual address, unique to each SVDU in a system, is set by the SCU when the system executes auto-configuration (described later). Under the individual addressing mode, only the addressed SVDU receives the command. If required, the addresses SVDU sends a response message to SCU UART microcontroller 205. Since only one SVDU responds to SCU UART microcontroller 205 at a time, only one receiver buffer of transceivers $230_1$ to $230_N$ needs be enabled. Furthermore, since SCU UART microcontroller 205 specifies the address of the individual SVDU, it knows which transmitter/receiver buffers of transceivers $230_1$ to $230_N$ should be enabled to transfer the message to/from the addressed SVDU.

Figure 3:
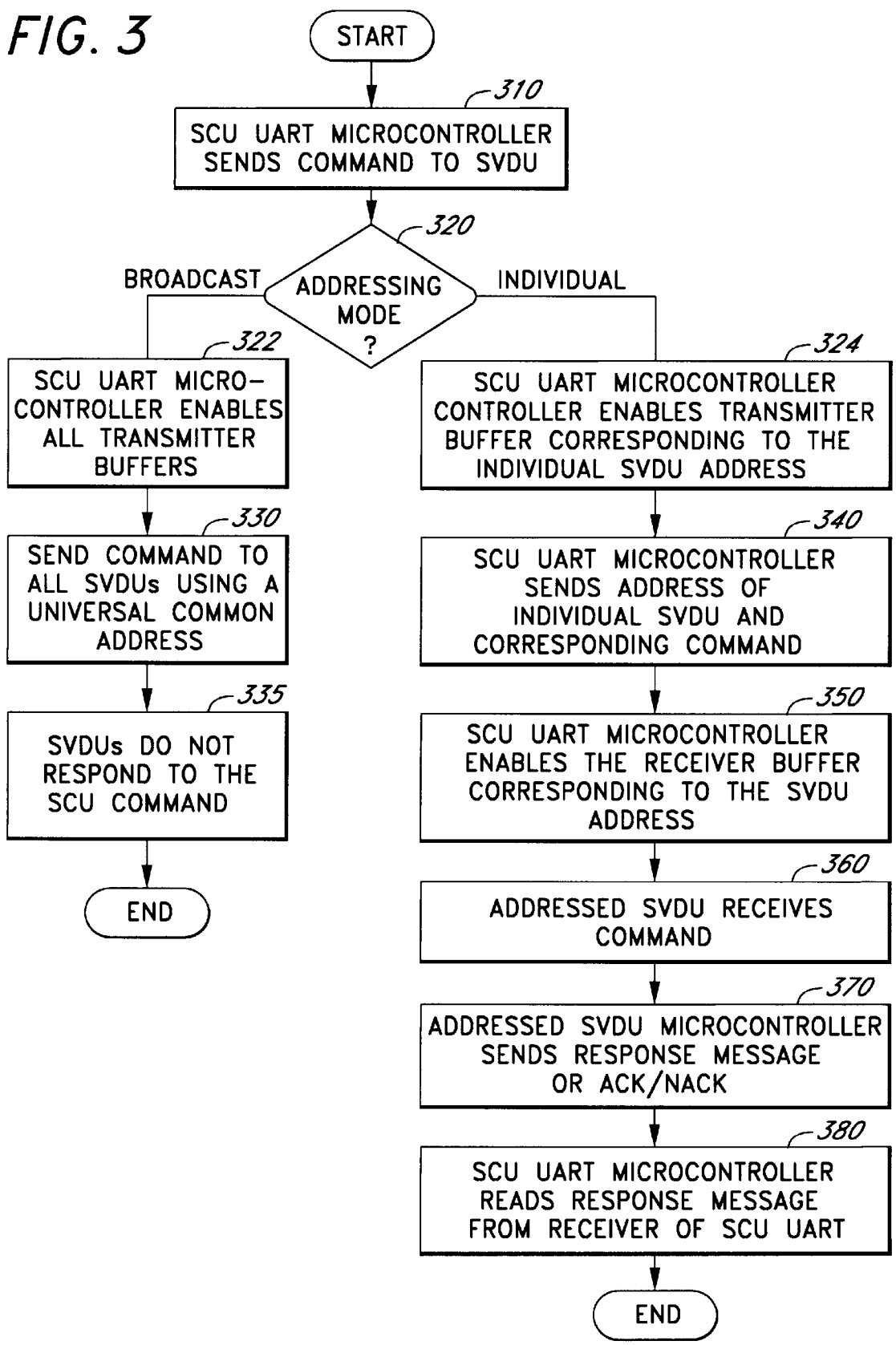
FIG. 3 is a flowchart illustrating one embodiment of the operation of the communication between the SCU and the SVDUs.

FIG. 3 shows a flowchart illustrating the operation of the communication between SCU UART microcontroller and the SVDUs. At START, the SCU UART microcontroller is ready to send a command to the SVDUs or SVDU (Step 310). A determination is made to determine the addressing mode (Step 320). If the addressing mode is broadcast, the SCU UART microcontroller enables the transmitter buffers to the SVDUs (Step 322), and sends the command to all SVDUs using a universal common address (Step 330). This universal common address may be a default address or may be assigned during configuration. In broadcast addressing, the SVDUs do not respond to the SCU UART microcontroller (Step 335).

If the addressing mode is individual, the SCU UART microcontroller enables the transmitter buffer to the addressed SVDU (Step 324), and sends the address of the specified SVDU and the corresponding command (Step 340). In anticipation of a response from the addressed SVDU, SCU UART microcontroller enables the buffer receiver corresponding to the SVDU address (Step 350). The addressed SVDU microcontroller receives the command from the SCU UART microcontroller (Step 360). The addressed SVDU microcontroller then sends a response to the received command (Step 370). This response may be a message for a specific request from the SCU such as status, test results, configuration data, and other operational parameters; or a message indicating whether the SVDU acknowledges (Ack) or does not acknowledge (Nack) the receipt of the command. Since the corresponding receiver buffer has been enabled, the SCU UART microcontroller reads the response message from the receiver of the SCU UART (Step 380). Each response normally has a predetermined size which is established in advance. The SCU UART microcontroller therefore knows how much it should read for a specific command.

Auto-Configuration

To increase reliability, the communication between SCU and SVDUs is auto-configurable. In other words, the SCU and the SVDUs are configured to communicate automatically without operator's intervention or jumper or switch settings. The auto-configuration feature avoids potential mistakes in setting the addresses by switches or other mechanical means.

The general approach is to allow the SCU to program the address and the configuration of each SVDU through an auto-configuration protocol.

Figure 4:
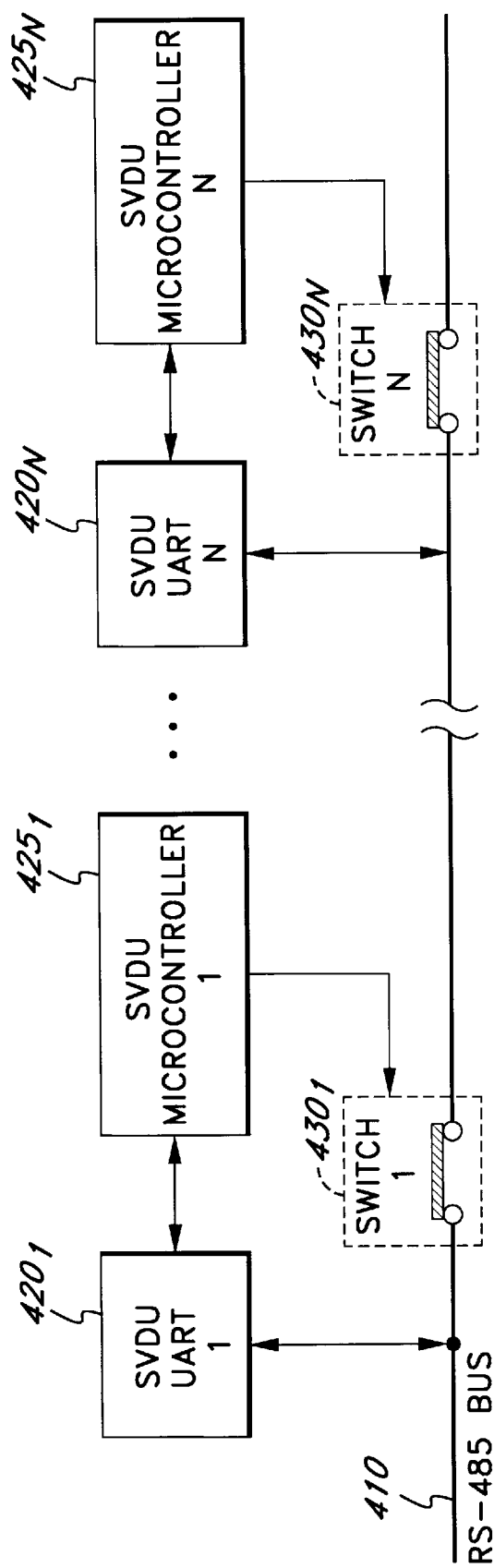
FIG. 4 shows one embodiment of the daisy-chain connection of the SVDUs for auto-configuration.

FIG. 4 shows one embodiment of this auto-configuration protocol. The SCU communicates with the SVDUs through a RS-485 serial bus 410. This serial bus establishes the communication link through SVDUs $420_1$ to $420_N$. The serial communication link is done in a daisy chain manner. SVDUs $420_1$ to $420_N$ contain Switches $430_1$ to $430_N$, respectively. Switches $430_1$ to $430_N$ are normally closed double pole double throw (DPDT) relays. Switches $430_1$ to $430_N$ are controlled by SVDU Microcontrollers $425_1$ to $425_N$, respectively. As a fail-safe feature, Switches $430_1$ to $430_N$ are normally closed so that if an SVDU does not power up for whatever reason, its corresponding Switch remains closed keeping the communication link unbroken.

FIG. 5 is a flowchart illustrating the auto-configuration communication protocol. At START, the SCU sends a System Reset command to all SVDUs (Step 510). This System Reset command informs all SVDUs that new individual addresses and configuration data are going to be sent. The new individual addresses and configuration data are stored in a non-volatile memory (e.g., EEPROM, FLASH). In response to this System Reset command, all SVDUs are reset to initial default conditions (Step 520). These initial default conditions include the same initial default address and open Switches. The initial default address is different than the Broadcast address discussed earlier. All Switches are open so that initially only the first SVDU in the daisy chain is connected to the SCU to receive further command from SCU. The Switch index k is set to 1 to indicate that $SVDU_1$ to connected to SCU.

Then, the SCU sends a Status Request command to the SVDU at the initial default address (Step 530). There is only one $SVDU_k$ corresponding to this initial default address and is connected to the SCU. This $SVDU_k$ responds to the SCU command (Step 540). Upon receipt of the response from SVDUk, SCU sends an Assign New Address command which specifies a new system-unique individual address to $SVDU_k$ (Step 550). This new individual address overwrites the initial default address given to $SVDU_k$ earlier. Once given this address, $SVDU_k$ responds only to this new individual address and does not respond to the initial default address. The SCU then sends configuration data to $SVDU_k$ (Step 560). These configuration data include information regarding the monitor, zone, or video selection and cable compensation for SVDUk. The SCU next sends a Store Current Settings command to SVDUk (Step 570). SVDU$_k$ stores all configuration data and its new Individual Address in its own non-volatile memory.

After the SVDU$_k$ finishes storing configuration data, the SCU sends a Close Switch command to SVDU$_k$ (Step 580). SVDU$_k$ closes its Switch to connect the bus link to the next SVDU in the chain. A determination is made to determine if all SVDUs have been configured (Step 590). If not, index k is incremented by 1 to indicate that the next SVDU in the daisy chain is going to be assigned a new individual address and new configuration data (Step 595). The process continues at Step 530. If all SVDUs have been assigned new Individual Addresses and configuration data, the auto-configuration is completed.

Heartbeat Timer

To increase the system reliability, the SCU issues a Heartbeat command to all SVDUs periodically to inform all SVDUs that the SCU is alive and functional. This Heartbeat command also contains information regarding whether the SVDU monitors are ON or OFF. The Heartbeat command is broadcast to all SVDUs using the broadcast addressing mode. If an SVDU fails to receive this Heartbeat command for a specified period of time, it assumes that some catastrophic failure, e.g., cabin decompression, SCU or serial bus failure, has occurred. In response, it will shut down its monitors. The Heartbeat command, therefore, acts like a watch-dog timer to increase system fault tolerance and system safety.

Another use of the Heartbeat command is to allow the SVDUs to re-boot after a momentary power failure. When there is a transient interruption in power, as when the aircraft is switched from ground to internal power, the Heartbeat command acts to ensure that the system recovers. Although the SCU is normally protected by a large capacitor which buffers it from transient power interruptions, the SVDUs are not similarly protected. A transient power failure, therefore, may cause the SVDUs to re-boot. The re-boot in itself does not cause any problem because all the SVDU configuration data are stored in non-volatile memory. However, upon re-boot, the SVDUs need to know if the monitors are ON or OFF. The periodic transmission of the Heartbeat command provides the SVDUs this information.

Table 1 shows a summary of commands sent from the SCU to the SVDUs. Some commands may be sent using either the broadcast or the individual addressing mode. Some commands require only one type of addressing mode. The commands are the message data sent from the SCU UART to the SVDUs.

TABLE 1

SCU–SVDU Command Summary

| Command from SCU to SVDU(s) | Command Length | Address Capability | Response To SCU (Non-Broadcast Only) |
| --- | --- | --- | --- |
| Turn Monitor 1 On | 3 Bytes | Bdcst/Ind | Ack/Nack |
| Turn Monitor 1 Off | 3 Bytes | Bdcst/Ind | Ack/Nack |
| Turn Monitor 2 On | 3 Bytes | Bdcst/Ind | Ack/Nack |
| Turn Monitor 2 Off | 3 Bytes | Bdcst/Ind | Ack/Nack |
| Turn Both Monitors On | 3 Bytes | Bdcst/Ind | Ack/Nack |
| Turn Both Monitors Off | 3 Bytes | Bdcst/Ind | Ack/Nack |
| Assign Monitor 1 to Video Source A | 3 Bytes | Bdcst/Ind | Ack/Nack |
| Assign Monitor 1 to Video Source B | 3 Bytes | Bdcst/Ind | Ack/Nack |
| Assign Monitor 1 to Video Source C | 3 Bytes | Bdcst/Ind | Ack/Nack |
| Assign Monitor 2 to Video Source A | 3 Bytes | Bdcst/Ind | Ack/Nack |
| Assign Monitor 2 to Video Source B | 3 Bytes | Bdcst/Ind | Ack/Nack |
| Assign Monitor 2 to Video Source C | 3 Bytes | Bdcst/Ind | Ack/Nack |
| Assign Monitor 1 to Zone 1 | 3 Bytes | Bdcst/Ind | Ack/Nack |
| Assign Monitor 1 to Zone 2 | 3 Bytes | Bdcst/Ind | Ack/Nack |
| Assign Monitor 1 to Zone 3 | 3 Bytes | Bdcst/Ind | Ack/Nack |
| Assign Monitor 1 to Zone 4 | 3 Bytes | Bdcst/Ind | Ack/Nack |
| Assign Monitor 2 to Zone 1 | 3 Bytes | Bdcst/Ind | Ack/Nack |
| Assign Monitor 2 to Zone 2 | 3 Bytes | Bdcst/Ind | Ack/Nack |
| Assign Monitor 2 to Zone 3 | 3 Bytes | Bdcst/Ind | Ack/Nack |
| Assign Monitor 2 to Zone 4 | 3 Bytes | Bdcst/Ind | Ack/Nack |
| Disable Monitor 1 | 3 Bytes | Individual | Ack/Nack |
| Disable Monitor 2 | 3 Bytes | Individual | Ack/Nack |
| Enable Monitor 1 | 3 Bytes | Individual | Ack/Nack |
| Enable Monitor 2 | 3 Bytes | Individual | Ack/Nack |
| Assign Zone 1 to Video Source A | 3 Bytes | Bdcst/Ind | Ack/Nack |
| Assign Zone 1 to Video Source B | 3 Bytes | Bdcst/Ind | Ack/Nack |
| Assign Zone 1 to Video Source C | 3 Bytes | Bdcst/Ind | Ack/Nack |
| Assign Zone 2 to Video Source A | 3 Bytes | Bdcst/Ind | Ack/Nack |
| Assign Zone 2 to Video Source B | 3 Bytes | Bdcst/Ind | Ack/Nack |
| Assign Zone 2 to Video Source C | 3 Bytes | Bdcst/Ind | Ack/Nack |
| Assign Zone 3 to Video Source A | 3 Bytes | Bdcst/Ind | Ack/Nack |
| Assign Zone 3 to Video Source B | 3 Bytes | Bdcst/Ind | Ack/Nack |
| Assign Zone 3 to Video Source C | 3 Bytes | Bdcst/Ind | Ack/Nack |
| Assign Zone 4 to Video Source A | 3 Bytes | Bdcst/Ind | Ack/Nack |
| Assign Zone 4 to Video Source B | 3 Bytes | Bdcst/Ind | Ack/Nack |
| Assign Zone 4 to Video Source C | 3 Bytes | Bdcst/Ind | Ack/Nack |
| Turn Zone 1 Monitors On | 3 Bytes | Bdcst/Ind | Ack/Nack |
| Turn Zone 1 Monitors Off | 3 Bytes | Bdcst/Ind | Ack/Nack |
| Turn Zone 2 Monitors On | 3 Bytes | Bdcst/Ind | Ack/Nack |
| Turn Zone 2 Monitors Off | 3 Bytes | Bdcst/Ind | Ack/Nack |
| Turn Zone 3 Monitors On | 3 Bytes | Bdcst/Ind | Ack/Nack |
| Turn Zone 3 Monitors Off | 3 Bytes | Bdcst/Ind | Ack/Nack |
| Turn Zone 4 Monitors On | 3 Bytes | Bdcst/Ind | Ack/Nack |
| Turn Zone 4 Monitors Off | 3 Bytes | Bdcst/Ind | Ack/Nack |
| Turn All Zones On | 3 Bytes | Bdcst/Ind | Ack/Nack |
| Turn All Zones Off | 3 Bytes | Bdcst/Ind | Ack/Nack |
| Heartbeat Message | Variable | Broadcast | — |
| Status Request | 3 Bytes | Individual | Ack/Nack |
| Start BITE (Intrusive Diagnostics) | 3 Bytes | Bdcst/Ind | Ack/Nack |
| Abort BITE | 3 Bytes | Bdcst/Ind | Ack/Nack |
| LRU BITE Status Request | 3 Bytes | Individual | BITE Status |

TABLE 1-continued

SCU–SVDU Command Summary

| Command from SCU to SVDU(s) | Command Length | Address Capability | Response To SCU (Non-Broadcast Only) |
|---|---|---|---|
| Read Physical Configuration Value | 3 Bytes | Individual | Configuration Data |
| Read Cable Compensation Data | 3 Bytes | Individual | Cable Comp Value |
| RESET to Factory Default Settings/Address | 3 Bytes | Bdcst/Ind | Ack/Nack |
| Assign New Address | Variable | Individual | Ack/Nack |
| Load Cable Compensation Value | Variable | Individual | Ack/Nack |
| Store Current Settings | 3 Bytes | Bdcst/Ind | Ack/Nack |
| Re-Set to Stored Settings | 3 Bytes | Bdcst/Ind | Ack/Nack |
| Close RS-485 Feedthrough Relay | 3 Bytes | Individual | Ack/Nack |
| Open RS-485 Feedthrough Relay | 3 Bytes | Bdcst/Ind | Ack/Nack |
| Decompression (all monitors off) | 3 Bytes | Broadcast | — |

Table 2 shows a summary of the response messages from the SVDUs to the SCU. The response messages are the message data transferred from the receiver buffers to the receiver in the SCU UART. Under the master-slave communication protocol, an SVDU does not transmit unsolicited data to the SCU. It only transmits in response to receiving an SCU command.

TABLE 2

SVDU–SCU Message Summary

| MESSAGE FROM SVDU TO SCU | MESSAGE LENGTH |
|---|---|
| Status Response | 7 Bytes |
| BITE Results Response | 5 Bytes |
| Configuration Data Response | 76 Bytes |
| Cable Compensation Value Response | 6 Bytes |
| Ack | 3 Bytes |
| Nack | 3 Bytes |

While this invention has been described with reference to illustrative embodiments, this description is not intended to be construed in a limiting sense. Various modifications of the illustrative embodiments, as well as other embodiments of the invention, which are apparent to persons skilled in the art to which the invention pertains are deemed to lie within the spirit and scope of the invention.

What is claimed is:

1. In a multipoint communication system having a processor for controlling a transfer of data between a control unit and a plurality of devices, a communication interface circuit comprising:

a control Universal Asynchronous Receiver and Transmitter (UART) coupled to the processor, said control UART having a transmitter and a receiver;

a plurality of transceivers coupled to said control UART for enabling and disabling the transfer of data, the transceivers having a corresponding number of transmitter buffers and receiver buffers, the transmitter buffers and receiver buffers providing isolatable communication links between the control unit and the plurality of devices;

an enable circuit coupled to the processor for enabling at most one of the receiver buffers at a time, the enable circuit being capable of enabling the plurality of the transmitter buffers in any combination in parallel; and a masking element coupled to the receiver buffers and the receiver for transferring a message data to the receiver when one of the receiver buffers is enabled.

2. The communication interface circuit of claim 1, further comprising:

a plurality of device processors for controlling the plurality of devices;

a plurality of device UARTs coupled to said plurality of device processors; and a plurality of device transceivers coupled to said plurality of device UARTs for enabling and disabling the transfer of data between the control unit and the plurality of devices.

3. The communication interface circuit of claim 1 wherein the masking element is an AND gate which interprets a data from a disabled receiver buffer as a logical 1.

4. The communication interface circuit of claim 1 wherein the masking element is an OR gate which interprets a data from a disabled receiver buffer as a logical 0.

5. The communication interface circuit of claim 1 wherein the masking element is a tri-state bus which masks out a data from a disabled receiver buffer.

6. The communication interface circuit of claim 1 wherein the enable circuit enables one of the transmitter buffers when the processor sends data through one of the communication links corresponding to said one of the transmitter buffers.

7. The communication interface circuit of claim 1 wherein the enable circuit further comprises a decoder which enables at most one receiver buffer.

8. The communication interface circuit of claim 1 wherein the processor sends a command to the plurality of devices using a broadcast addressing mode.

9. The communication interface circuit of claim 1 wherein the processor sends a command to one of the plurality of devices using an individual addressing mode.

10. The communication interface circuit of claim 7 wherein a device processor sends a response message to the processor when it receives a command from the processor using the individual addressing mode.

11. The communication interface circuit of claim 1 wherein the processor is a microcontroller.

12. The communication interface circuit of claim 2 wherein each of the device processors is a microcontroller.

13. A method of providing efficient isolatable multipoint communication in a system having a processor for controlling a transfer of data between a control unit and a plurality of devices, said method comprising steps of:

controlling a Universal Asynchronous Receiver and Transmitter (UART) by the processor;

configuring a plurality of receiver buffers such that at most one receiver buffer is enabled at a time;

configuring a plurality of transmitter buffers such that the plurality of transmitter buffers is enabled in any combination in parallel; and masking a plurality of data from the receiver buffers such that only a message data from an enabled receiver buffer is transferred to the UART.

14. The method of claim 13 further comprises a step of enabling at least one of a plurality of transmitter buffers when the processor transmits data to a communication link corresponding to said at least one of the plurality of transmitter buffers.

15. The method of claim 13 further comprises the steps of:

addressing said plurality of devices; and sending a command to said plurality of devices.

16. The method of claim 15 wherein the step of addressing is one of a broadcast addressing and an individual addressing.

17. The method of claim 16 further comprises a step of receiving a response message from an addressed device when the step of addressing is the individual addressing.

18. The method of claim 13 wherein the step of configuring further comprises steps of
connecting a plurality of receiver enable control signals to the plurality of receiver buffers to a decoder; and
generating a bit pattern to the decoder for enabling at most one of the plurality of receiver buffers.

19. The method of claim 13 wherein the step of configuring further comprises steps of
connecting a plurality of receiver enable control signals corresponding to said plurality of receiver buffers to an input/output (I/O) port; and
generating a bit pattern to the I/O port for enabling at most one of the plurality of receiver buffers.

20. A multipoint communication system comprising:
a processor; and
a communication interface circuit coupled to the processor for controlling a transfer of data between a control unit and a plurality of devices, the communication interface circuit comprising:
a control Universal Asynchronous Receiver and Transmitter (UART) coupled to the processor, said control UART having a transmitter and a receiver;
a plurality of transceivers coupled to said control UART for enabling and disabling the transfer of data, the transceivers having a corresponding number of transmitter buffers and receiver buffers, the transmitter buffers and receiver buffers providing isolatable communication links between the control unit and the plurality of devices;
an enable circuit coupled to the processor for enabling at most one of the receiver buffers at a time, the enable circuit being capable of enabling the plurality of the transmitter buffers in any combination in parallel; and
a masking element coupled to the receiver buffers and the receiver for transferring a message data to the receiver when one of the receiver buffers is enabled.

* * * * *